(12) United States Patent
Oakey et al.

(10) Patent No.: US 12,030,918 B2
(45) Date of Patent: Jul. 9, 2024

(54) FIBRIN PARTICLES AND METHODS OF FORMING FIBRIN PARTICLES

(71) Applicant: UNIVERSITY OF WYOMING, Laramie, WY (US)

(72) Inventors: John Oakey, Laramie, WY (US); Alan Stenquist, Laramie, WY (US)

(73) Assignee: UNIVERSITY OF WYOMING, Laramie, WY (US)

( * ) Notice: Subject to any disclaimer, the term of this patent is extended or adjusted under 35 U.S.C. 154(b) by 372 days.

(21) Appl. No.: 17/112,661

(22) Filed: Dec. 4, 2020

(65) Prior Publication Data

US 2021/0171587 A1 Jun. 10, 2021

Related U.S. Application Data

(60) Provisional application No. 62/944,399, filed on Dec. 6, 2019.

(51) Int. Cl.
*A61K 38/00* (2006.01)
*C07K 14/435* (2006.01)
*C07K 14/75* (2006.01)

(52) U.S. Cl.
CPC ............ *C07K 14/435* (2013.01); *C07K 14/75* (2013.01)

(58) Field of Classification Search
CPC .................. C07K 14/435; C07K 14/75; C12Y 304/21005
See application file for complete search history.

(56) References Cited

U.S. PATENT DOCUMENTS

| | | | | |
|---|---|---|---|---|
| 2003/0091559 A1* | 5/2003 | Woolverton | ........... | A61L 24/106 424/94.64 |
| 2008/0044852 A1* | 2/2008 | Kanayinkal | ............ | A61K 35/16 435/68.1 |
| 2010/0255059 A1* | 10/2010 | Marquez | ................ | A61K 35/28 424/93.73 |
| 2020/0093896 A1* | 3/2020 | Debraize | .............. | A61K 47/183 |
| 2021/0169813 A1* | 6/2021 | Muhamed | ................ | A61L 27/50 |

FOREIGN PATENT DOCUMENTS

| | | | | |
|---|---|---|---|---|
| WO | WO-2013185097 A1 * | 12/2013 | ......... | A61K 38/1825 |
| WO | WO-2017091601 A1 * | 6/2017 | .......... | B01J 19/0093 |

OTHER PUBLICATIONS

C.H. Park et al. (2018), Fibrin-Based Biomaterial Applications in Tissue Engineering and Regenerative Medicine, in: Noh, I. (eds) Biomimetic Medical Materials. Advances in Experimental Medicine and Biology, vol. 1064 Springer, Singapore, https://doi.org/10.1007/978-981-13-0445-3_16.
A. Noori et al. "A review of fibrin and fibrin composites for bone tissue engineering." Int. J. Nanomedicine, Jul. 12, 2017; 12:4937-4961, https://doi.org/10.2147/IJN.S124671.
J.W. Weisel et al. "Mechanisms of fibrin polymerization and clinical implications" Blood, Mar. 7, 2013; 121(10): 1712-19, https://doi.org/10.1182/blood-2012-09-306639.
S. Yesudasan, wt al. "Fibrin polymerization simulation using a reactive dissipative particle dynamics method." Biomech Model Mechanobiol 17, 1389-1403 (2018), https://doi.org/10.1007/s10237-018-1033-8.
Sarah E. Stabenfeldt et al. "Engineering fibrin polymers through engagement of alternative polymerization mechanisms", Biomaterials, vol. 33, Issue 2, 2012, pp. 535-544, https://doi.org/10.1016/j.biomaterials.2011.09.079.
N.A. Kurniawan et al., "Buffers Strongly Modulate Fibrin Self-Assembly into Fibrous Networks", Langmuir 2017, 33, 6342-6352, https://doi.org/10.1021/acs.langmuir.7b00527.
K.B. Neeves et al. "Thrombin flux and wall shear rate regulate fibrin fiber deposition state during polymerization under flow", Biophys J., Apr. 7, 2010; 98(7):1344-52, https://doi.org/10.1016/j.bpj.2009.12.4275.
E.P. Sproul, (2018), "Controlling Fibrin Network Morphology, Polymerization, and Degradation Dynamics in Fibrin Gels for Promoting Tissue Repair" In: Chawla, K. (eds) Biomaterials for Tissue Engineering. Methods in Molecular Biology, vol. 1758. Humana Press, New York, NY, https://doi.org/10.1007/978-1-4939-7741-3_7.
B. Blombäck et al. "Fibrin in human plasma: Gel architectures governed by rate and nature of fibrinogen activation", Thrombosis Research, vol. 75, Issue 5, 1994, pp. 521-538, https://doi.org/10.1016/0049-3848(94)90227-5.
J. Yu et al. "Real-time measurement of thrombin generation using continuous droplet microfluidics", Biomicrofluidics, Sep. 3, 2014; 8(5):052108, https://doi.org/10.1063/1.4894747.

* cited by examiner

*Primary Examiner* — Aradhana Sasan
*Assistant Examiner* — Mercy H Sabila
(74) *Attorney, Agent, or Firm* — Patterson + Sheridan, LLP

(57) ABSTRACT

The present disclosure generally relates to compositions comprising fibrin and to methods of forming such compositions. In an embodiment, a method of forming fibrin particles is provided. The method includes introducing a buffer, a fibrinogen solution, and a thrombin solution to a first end of a microfluidic device to form a mixture, the buffer comprising one or more amino acids. The method further includes contacting the mixture with a fluorocarbon oil and a surfactant to form fibrinogen-containing particles, and applying positive pressure to the microfluidic device to cause the fibrinogen-containing particles to flow towards a second end of the microfluidic device. The method further includes collecting the fibrinogen-containing particles at the second end of the microfluidic device; and polymerizing the fibrinogen-containing particles to form fibrin particles.

20 Claims, 4 Drawing Sheets

FIBRIN PARTICLES AND METHODS OF FORMING FIBRIN PARTICLES

CROSS-REFERENCE TO RELATED APPLICATIONS

This application claims priority to U.S. Provisional Patent Application No. 62/944,399, filed Dec. 6, 2019, which is herein incorporated by reference in its entirety.

FIELD

The present disclosure generally relates to compositions comprising fibrin and to methods of forming such compositions.

BACKGROUND

Fibrin is the provisional protein matrix that forms at the site of injury or in the blood in response to stress, and is implicated in various diseases such as cardiovascular disease. Fibrin forms by thrombin-catalyzed polymerization of fibrinogen, and the polymerized fibrin scaffold then clots at the wound site. The structure and properties of the fibrin scaffold generally govern the progress and outcomes of cardiovascular disease, stroke, and trauma. Fibrin also serves as an interim matrix to recruit cells to clot sites needed for the regeneration of tissue. At the clot site, the cells secrete extracellular molecules such as collagen to promote wound healing.

While the rapid polymerization of fibrin is advantageous for maintaining hemostasis, it prevents widespread use of fibrin as a scaffold for, e.g., tissue engineering. In addition, the low solubility of fibrinogen/fibrin, and the heat sensitivity of fibrinogen and thrombin, further challenges these efforts. To mitigate such issues, conventional methods of forming fibrin maintain solutions of fibrinogen and thrombin at temperatures near freezing, which drives up manufacturing costs and is impractical for production scale-up. Other conventional methods employ heavy mineral oils to slow down the polymerization of fibrinogen. However, a wash step using harsh solvents is required to remove such oils, killing most cells and proteins including fibrinogen, thrombin, and fibrin. Consistent sizing and the lack of desired mechanical properties of fibrin particles needed for blood clotting present an additional hurdle to state-of-the-art methods of forming fibrin particles.

There is a need for new and improved methods of forming compositions comprising fibrin and to methods of forming such compositions that overcome these and other deficiencies.

SUMMARY

The present disclosure generally relates to compositions comprising fibrin and to methods of forming such compositions.

In an embodiment, a method of forming fibrin particles is provided. The method includes introducing a buffer, a fibrinogen solution, and a thrombin solution to a first end of a microfluidic device to form a mixture, the buffer comprising one or more amino acids. The method further includes contacting the mixture with a fluorocarbon oil and a surfactant to form fibrinogen-containing particles, and applying positive pressure to the microfluidic device to cause the fibrinogen-containing particles to flow towards a second end of the microfluidic device. The method further includes collecting the fibrinogen-containing particles at the second end of the microfluidic device; and polymerizing the fibrinogen-containing particles to form fibrin particles.

In another embodiment, a method of forming fibrin particles is provided. The method includes co-flowing a buffer, a fibrinogen solution, and a thrombin solution into an introduction area of a fluidic channel to form an aqueous phase, the fluidic channel further comprising a contacting area and a mixing area, wherein the buffer comprises one or more amino acids, and the fibrinogen solution, the buffer, or both, comprise one or more inhibitors. The method further includes causing the aqueous phase to flow from the introduction area at a first end of the fluidic channel to the mixing area at a second end of the fluidic channel, the contacting area in a location between the introduction area and mixing area. The method further includes contacting the aqueous phase with an oil phase at the contacting area to form a dispersion of the aqueous phase in the oil phase, the oil phase comprising a fluorocarbon oil and a surfactant. The method further includes causing the dispersion to flow from the contacting area to the mixing area, collecting the dispersion at the second end of the fluidic channel, and heating the dispersion under conditions effective to form fibrin particles.

In another embodiment, a method of forming fibrinogen-containing particles is provided. The method includes co-flowing a buffer, a fibrinogen solution, a thrombin solution to form an aqueous phase, wherein an amount of fibrinogen in the fibrinogen solution is from about 5% w/v to about 25% w/v, the buffer comprises one or more amino acids, and the fibrinogen solution, the buffer, or both, comprise one or more inhibitors. The method further includes contacting the aqueous phase with an oil phase comprising a surfactant to form fibrinogen containing droplets.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

DETAILED DESCRIPTION

Figure 1A:
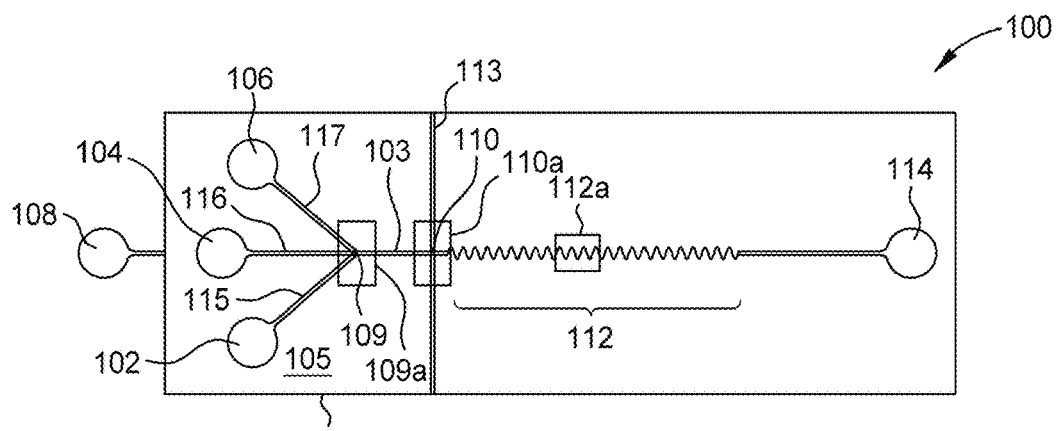
FIG. 1A is a schematic of an example apparatus for forming particles comprising fibrinogen, among other components, according to at least one embodiment of the present disclosure.

The present disclosure generally relates to compositions comprising fibrin and to methods of forming such compositions. The inventors have found new and improved methods of forming fibrin particles (e.g., microparticles and nanoparticles) using a microfluidic droplet generator. The compositions can include fibrin particles and supraphysiological fibrin particles useful for, e.g., tissue engineering, among other applications.

Briefly, and in some examples, the fibrin particles are formed by introducing fibrinogen, thrombin, an inhibitor, a buffer (which includes amino acids), and an oil to a microfluidic device and generating a droplet. Flow rates of these components can be adjusted to tune, e.g., the fibrinogen content of the droplet generated and/or the size of the droplet generated. These droplets, containing fibrinogen in a stable matrix with thrombin and other components, can then be collected from the microfluidic device. In some embodiments, the droplets are subjected to polymerization via, e.g., incubation to form fibrin particles Embodiments described herein enable, e.g., production of consistently-sized fibrin particles with useful and robust mechanical properties. Such particles can also be composed of supraphysiological levels of fibrin (e.g., such as greater than about 1% weight/volume (w/v)), which may aid in providing the fibrin particles with their robust mechanical properties. In further contrast to conventional processes of forming fibrin particles, the fibrinogen, thrombin, and reagents do not need to be maintained at cold temperatures during fibrin-particle production. Moreover, the inventors have found methods to increase the solubility of fibrinogen. Typically, fibrinogen is difficult to keep soluble at concentrations over about 2% w/v in conventional buffers. Such low solubility limits the ability to modulate properties of the fibrin network by changing the mass fraction in solution. As described herein, a buffered solution that includes one or more amino acids can be utilized to solubilize fibrinogen at much higher concentrations than those known in the art. In some examples, solutions of about 25% w/v fibrinogen or more can be created in minutes, even with using cold reagents, and with little or no precipitation. Such solutions enable supraphysiological levels of fibrinogen to be in solution and a high dynamic range in fibrin content enables altering of the mechanical properties of the particle by adjusting the mass fraction of fibrin.

In addition, embodiments described herein are useful for controlling the polymerization of fibrinogen to fibrin. Here, the use of an amino-acid containing buffer is utilized to prevent, or at least mitigate, fibrin formation until the particles/droplets exit the microfluidic device and are subjected to incubation conditions. These amino acids include charged amino acids, which refers to amino acids having side chain groups that are charged at certain pH levels (e.g., charged at a physiologically relevant pH or about 7. Such charged amino acids include negatively charged amino acids (e.g., aspartic acid and/or glutamic acid) and positively charged amino acids (e.g., lysine, arginine, and/or histidine). The side chains of aspartic acid and glutamic acid are negatively charged at pH levels above the pK of their amino acid side chain group. In contrast, and for lysine, arginine, and/or histidine, their amino acid side chain group is positively charged at pH levels below the pK of the side chain group.

While not wishing to be bound by theory, it is believed that the charged amino acids replace the hydration shell/water that is interacting with the fibrinogen and thrombin proteins, thereby increasing the free energy of aggregation of fibrinogen to prevent or substantially reduce aggregation and/or polymerization of fibrinogen. That is, the charged amino acids keep the fibrinogen stable such that fibrin is not formed in, e.g., the microfluidic device. In some embodiments, the microfluidic device is substantially free (e.g., less than 10% of the fibrinogen is consumed to form fibrin in the microfluidic device, such as less than 5%) of fibrin while forming the particles as determined by immunofluorescence.

Embodiments herein also enable the generation of supraphysiological levels of fibrin (e.g., greater than about 1%). Such levels of fibrin are useful in cases where increased blood clotting is needed. Sonicated fibrin is the conventional route to provide supplemental blood clotting. However, sonication produces fibrin particles of various dimensions and sizes, resulting in poor mechanical properties and limiting their use.

The following illustrative, but non-limiting, examples are not intended to limit the scope of aspects of the present disclosure. In addition, "droplets" and "particles" are used interchangeably unless specified to the contrary or the context clearly indicates otherwise. Further, while the present disclosure refers to "microparticles" will be appreciated that the disclosure may be applied to particles having a smaller size (e.g., "nanoparticles") or to particles having a larger size (e.g., "macroparticles"). Also, while examples and embodiments are described herein with reference to encapsulation of components (e.g., fibrinogen, thrombin, fibrin, etc.), it is contemplated that the components can be dispersed, retained, or otherwise held in or by the particle. For example, example apparatus 100 and methods described herein can be utilized to form, e.g., fibrinogen-encapsulated particles or fibrinogen-dispersed particles.

EXAMPLES

Example Apparatus

Figure 1B:
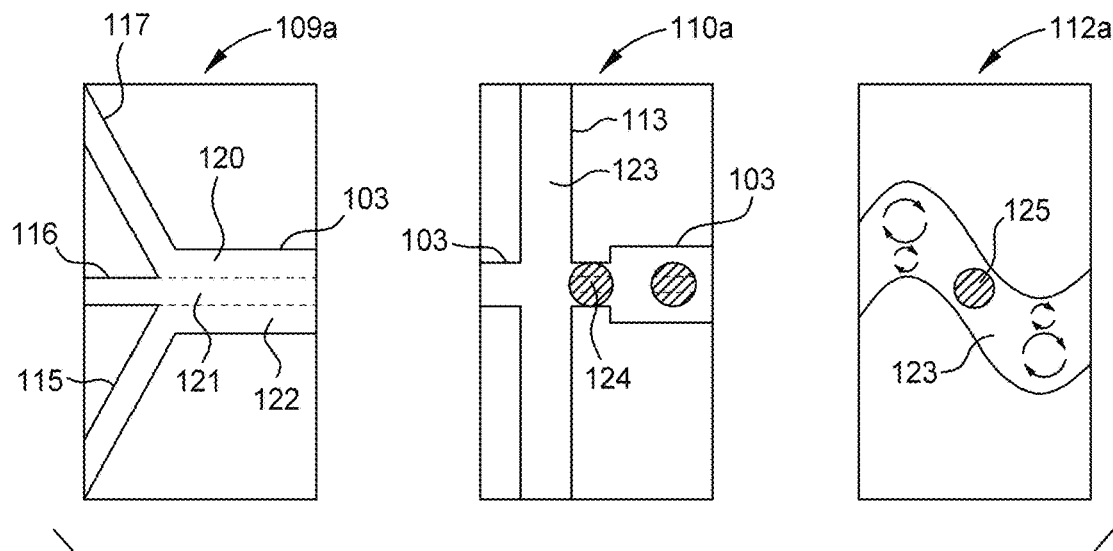
FIG. 1B is a pictorial representation of selected elements of the example apparatus shown in FIG. 1A according to at least one embodiment of the present disclosure.

FIG. 1A is a schematic of an example apparatus 100 for forming droplets, or particles (e.g., microparticles), comprising fibrinogen, among other components, according to at least one embodiment of the present disclosure. FIG. 1B is a pictorial representation of selected elements of the example apparatus shown in FIG. 1A, and FIGS. 1C-1E shows exemplary images of fluids and materials flowing through the example apparatus shown in FIG. 1A (Imaged with a Phantom high-speed camera; fluorescent tracer). After collecting the fibrinogen-containing particles, or droplets, from the apparatus 100, the fibrinogen-containing particles/droplets can be, e.g., heated/incubated to form fibrin particles.

Apparatus 100 includes a microfluidic device 101. The microfluidic device includes an introduction area 105, a contacting area 110, and a mixing area 112. Briefly, and as discussed below, a fibrinogen solution, a thrombin solution, and a buffer (which are aqueous solutions) are introduced to the microfluidic device 101 in the introduction area 105; an oil phase contacts the aqueous solutions and buffer in the contacting area 110; and after contact, the aqueous phase dispersed in the oil phase travels through mixing area 112.

The microfluidic device 101 includes a fluidic channel 103. In at least one embodiment, the fluidic channel 103 has a diameter of micrometers (μm) to millimeters (mm). For example, the fluidic channel 103 has a diameter from about 1 μm to about 2 mm and/or a depth of about 1 μm to about 2 mm. The microfluidic device 101 has an opening 102 for introducing a fibrinogen solution, an opening 104 for introducing a buffer (which includes amino acids and an inhibitor), and an opening 106 for introducing a thrombin solution. A channel 115 fluidly couples opening 102 to the fluidic channel 103 such that fibrinogen solution can be introduced to the fluidic channel 103. Similarly, channel 116 fluidly couples opening 104 to the fluidic channel 103 and channel 117 fluidly couples opening 106 to the fluidic channel 103 such that the buffer and thrombin solution can be introduced to the fluidic channel 103. The channels 115, 116, and 117 can, independently, have the same or different dimensions. For example, the channel 115 can have a larger or smaller diameter than that of channel 116 and/or channel 117. In some embodiments, channels 115, 116, and 117 can, independently, have a diameter that is larger than, smaller than, or the same dimensions as fluidic channel 103. The fibrinogen solution and thrombin solution are typically introduced to the microfluidic device as aqueous solutions in, e.g., a buffer.

The microfluidic device 101 includes another opening 108 for introducing a fluorocarbon oil. The fluorocarbon oil serves to encapsulate the cargo (e.g., fibrinogen and thrombin, among other components) in a single particle/droplet. As described below, the fluorocarbon oil travels through channel 113 and pinches off the fibrinogen, buffer, and thrombin to form droplets at a contacting area 110. Channel 113 can have the same or different dimensions as channels 115, 116, and 117. Channel 113 can have a larger or smaller diameter than that of channels 115, 116, and 117, independently, and have a diameter that is larger than, smaller than, or the same dimensions as fluidic channel 103.

The fluorocarbon oil is also an effective diffusion barrier that enables retention of the cargo and helps mitigate fusion of the particles/droplets. Suitable fluorocarbon oils include Novec™ (3M Company) and Fluorinert™ (3M Company oils), such as Novec™ 7500, Fluorinert™ FC-40, Fluorinert™ FC-70, and Fluorinert™ FC-770. The fluorocarbon oil can contain additives such as surfactants, for example, fluorosurfactants. Illustrative, but non-limiting, examples of fluorosurfactants include Picosurf® (Dolomite Microfluidics), such as Picosurf™ 1 and Picosurf™ 2, RAN Biotech 008-FluoroSurfactant, HFE 7500, and Krytox 157. In some embodiments, the concentration of fluorosurfactant in the fluorocarbon oil ranges from about 2% w/v to about 5% w/v, such as from about 3% w/v to about 4% w/v.

Figure 1C:
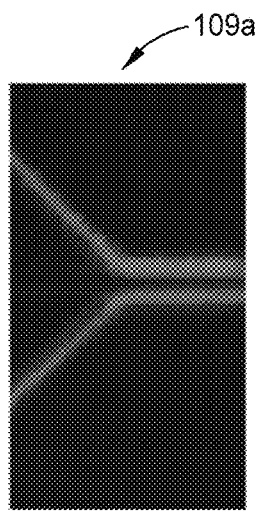
FIG. 1C is an exemplary image of materials flowing through the example apparatus shown in FIG. 1A according to at least one embodiment of the present disclosure.

Tubings, or other suitable apparatus, are coupled to the individual openings 102, 104, 106, and 108 to enable introduction of the fibrinogen solution, buffer, thrombin solution, and fluorocarbon oil to the fluidic channel 103. The fibrinogen solution, buffer, and thrombin solution meet at a junction 109 and flow through the fluidic channel 103 in a co-stream. As shown in FIG. 1B, 109a is a pictorial representation of this co-streaming channel where the streams of fibrinogen solution 122, buffer 121, and thrombin solution 120 flow through the fluidic channel 103. As shown in FIG. 1C, the buffer 121 creates a layer of separation between the fibrinogen solution 122 and the thrombin solution 120, even though the solutions are co-streaming in a single channel. Separation of the stream of fibrinogen solution 122 and the stream of thrombin solution 120 by use of the buffer prevents the streams of the fibrinogen solution and thrombin solution from mixing until the droplets are formed as described below. The buffer also prevents early fibrin formation which can clog the microfluidic device and/or cause reduced homogeneity of the generated particles/droplets.

Figure 1D:
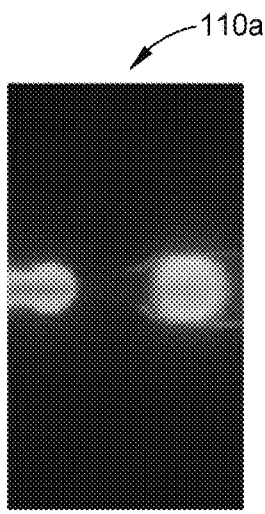
FIG. 1D is an exemplary image of materials flowing through the example apparatus shown in FIG. 1A according to at least one embodiment of the present disclosure.

The fluidic channel 103 includes the contacting area 110 where the fluorocarbon oil pinches off the fibrinogen, buffer, and thrombin to form droplets. The contacting area 110 includes a junction. 110a of FIG. 1B is a pictorial representation of contacting area 110 showing droplets 124, which include fibrinogen solution, buffer, and thrombin solution, being pinched off by the fluorocarbon oil 123 at or near the junction. The fluorocarbon oil, as discussed above, travels through channel 113, while the aqueous phase (fibrinogen solution, buffer, and thrombin solution) travels through channel 103. A dispersion is formed when the aqueous phase contacts the oil phase such that droplets 124 are formed in the oil phase. As shown in FIG. 1D, droplets 124 pinch off at a suitable rate upon sufficient contact with the oil phase.

Figure 1E:
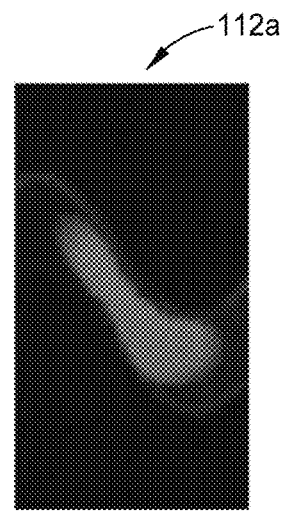
FIG. 1E is an exemplary image of materials flowing through the example apparatus shown in FIG. 1A according to at least one embodiment of the present disclosure.

After the droplets are formed, the dispersion of the droplets in the oil phase is caused to flow (by, e.g., positive pressure) through the mixing area 112 of the fluidic channel 103 and towards fluidic channel exit 114. Here, the droplets 124 travel along the mixing area 112 such that the droplets become sufficiently mixed to form droplets 125. The fluidic channel 103 of the mixing area 112 has a serpentine shape/design, the length of which enables, e.g., sufficient mixing of the fibrinogen solution, buffer, and thrombin solution in the fluorocarbon oil. 112a of FIG. 1B is a pictorial representation of a portion of mixing area 112 where components within droplets 124 sufficiently mix, while traveling through mixing area 112, to form droplets 125. FIG. 1E is an image of the fibrinogen-containing droplets/particles traveling through the serpentine fluidic channel of the mixing area.

After sufficient mixing, the dispersion of the fibrinogen-containing droplets/particles in the oil move toward the fluidic channel exit 114 where they are collected for further processing and/or analysis. Other materials (buffer, excess components, oil, etc.) exit the fluidic channel exit 114 along with the droplets/particles. Upon exit, the droplets/particles can be purified, or otherwise isolated, from the other materials exiting the apparatus 100. The dispersion (or a portion of the dispersion) can be heated, in e.g., an incubator, under conditions effective to form fibrin particles to form fibrin particles. Conditions effective to form fibrin particles can include a temperature of greater than room temperature, such as about 30° C. or more, such as from about 30° C. to about 37° C.; and/or a time of polymerization of about 1 hour or more such as from about 3 hours to about 24 hours, such as from about 5 hours to about 15 hours.

Movement of the various materials from the one or more openings 102, 104, 106, and 108 to the fluidic channel exit 114 is controlled by, e.g., a pumping mechanism, a pressure regulation system (such as those available from Fluigent), and/or electrodes. Such elements controlling the movement can be placed at opposing ends of or along various regions along a length of the fluidic channel 103. Design parameters to effectively form droplets/particles at desired concentrations include the length and width of the channels, the spacing between the channels and/or openings, and the flow rates of fluid flowing through the microfluidic device.

Conventional uses of microfluidic devices is challenged by the gelation of fibrinogen. However, and in some embodiments, the gelation of fibrinogen can be modulated by keeping the entire system cold (e.g., from about 2° C. to about 6° C.) and reducing the enzyme activity of thrombin. Alternatively or additionally, and in some embodiments, the action of fibrinogen can be modulated by use of an inhibitor, e.g., bivalirudin. Bivalirudin can tightly bind to the active site of thrombin, inactivating the enzyme and preventing conversion of fibrinogen to fibrin. In some embodiments, the ratio of bivalirudin to thrombin can be adjusted. In at least one embodiment the ratio of bivalirudin to thrombin is about 500:1 to about 2,000:1, such as from about 750:1 to about 1,750:1, such as from about 1,000:1 to about 1,500:1, such as from about 1,100:1 to about 1,300:1, such as about 1,250:1. By adjusting the ratio of bivalirudin to thrombin, the gelation of fibrinogen can be delayed from about several minutes to over about an hour.

Alternatively or additionally, and in some embodiments, the action of fibrinogen can be modulated, the gelation of fibrinogen (and formation of fibrin) can be delayed/modulated by use of buffers described herein. As described below, the buffers include various components that stabilize fibrinogen, thereby delaying formation of fibrin.

This tight control over the gelation of fibrinogen enables, e.g., co-streaming of fibrinogen and thrombin through small microfluidic channels without the risk of clogging, and the creation of fibrinogen-containing particles and fibrin particles at room temperature. By solubilizing large amounts of fibrinogen, many of the limitations of this material as well as its use in microfluidic devices can be overcome, as further discussed herein.

Example Buffer

Fibrinogen tends to self-aggregate at concentrations in saline solution over about 1% w/v. This low solubility limits large concentrations of fibrinogen being present in solution. The driving force of this self-aggregation is the favorable free energy association in reducing polar solvent accessible area on hydrophobic regions. Hydrophobic regions on one protein interact with exposed hydrophobic regions on another protein, causing aggregation. The inventors have found that by surrounding fibrinogen with buffers described herein, the fibrinogen monomers can be stabilized, reducing the potential intermediate fibrinogen conformations that may expose hydrophobic residues and lead to aggregation. In addition, the buffers need no special care, mixing, etc., and the fibrinogen does not precipitate once in solution, even when chilled or frozen.

In some embodiments, the buffer is an aqueous buffer with one or more charged amino acids, one or more inhibitors, one or more salts, or combinations thereof. The charged amino acids include positively-charged amino acids (e.g., arginine (Arg), lysine (Lys), histidine (His), or combinations thereof) and/or negatively-charged amino acids (e.g., aspartic acid (Asp) and/or glutamic acid (Glu)). The buffer can include both positively-charged amino acid(s) and negatively-charged amino acid(s), such as arginine and glutamic acid. The concentration of the one or more amino acids can range from about 10 millimolar (mM) to about 100 mM, such as from about 15 mM to about 95 mM, such as from about 20 mM to about 90 mM, such as from about 25 mM to about 85 mM, such as from about 30 mM to about 80 mM, such as from about 35 mM to about 75 mM, such as from about 40 mM to about 70 mM, such as from about 45 mM to about 65 mM, such as from about 50 mM to about 60 mM. In at least one embodiment, the concentration of the one or more amino acids in the buffer is from about 50 mM to about 75 mM, such as about 50 mM. When more than one amino acid is utilized, equimolar amounts of the amino acids can be used or differing amounts of the amino acids can be used.

The buffer can include additives such as polymerization inhibitors or thrombin inhibitors. As a non-limiting example, bivalirudin, which is a reversible inhibitor of thrombin, can be utilized. The concentration of the one or more inhibitors in the buffer can be about 0.01 mg/mL or more, such as from about 0.02 mg/mL to about 0.1 mg/mL, such as from about 0.04 mg/mL to about 0.08 mg/mL, such as from about 0.05 mg/mL to about 0.06 mg/mL. In at least one embodiment, the concentration of the one or more inhibitors in the buffer is about 0.05 mg/mL.

The buffer can include salts, such as alkali metal salts and alkaline earth metal salts. Corresponding anions for the salts include, but are not limited to phosphate ion, and chlorine ion. In some examples the buffer is, e.g., a phosphate buffered saline (PBS) and/or a (4-(2-hydroxyethyl)-1-piperazineethanesulfonic acid) (HEPES) containing aqueous solution. The pH of the buffer ranges from about 7 to about 10, such as from about 7.5 to about 9.5, such as from about 8 to about 9. In at least one embodiment, the pH of the buffer is about 9. The pH of the buffer can be adjusted by use of suitable acids or bases such as hydrochloric acid and sodium hydroxide. In some embodiments, the buffer is a PBS buffer (pH of about 9) that includes about 50 mM arginine and about 50 mM glutamic acid is utilized.

As discussed above, fibrinogen is difficult to keep soluble at concentrations over about 1 weight percent in most common buffers. Fibrinogen's inherent solubility limits the ability to modulate the fibrin network properties by changing the mass fraction in solution as can be done with synthetic polymers. As opposed to conventional buffers which are only able to solubilize less than about 2% w/v fibrinogen, the buffers described herein can solubilize greater than about 2% w/v fibrinogen, such as from about 2% w/v to about 25% w/v of fibrinogen, such as from about 5% w/v to about 20% w/v. Such fibrinogen solutions can be created in minutes, even with using cold reagents, and with no precipitation. As such, the solubility of fibrinogen is no longer limiting. In addition, the buffer through, e.g., chemical interactions and/or physical interactions, keeps the fibrinogen away from the thrombin, thereby preventing or mitigating polymerization during droplet/particle formation and mixing while in the microfluidic device.

Example Method of Forming Fibrin Particles

Embodiments of the present disclosure also relate to methods of forming particles. The particles, or droplets, include fibrinogen, buffer, and thrombin. Polymerization of such particles then forms fibrin particles. The fibrin particles can be formed by the following illustrative, non-limiting, procedure.

(a) Create the buffer. For this example, the buffer is a ~50 mM Arg/Glu (arginine/glutamic acid) buffered solution at a pH of about 7 to about 7.5 (such as about 7.2), but can be a pH up to about 9-10.

In some embodiments, the buffer used for the microfluidic device can contain additives such as one or more thrombin inhibitors, e.g., bivalirudin. The amount of inhibitor that can be proportional to the amount of inhibitor added to the fibrinogen solution. For example, the inhibitor can be added to the buffer at about 0 to about 0.5× the amount of the inhibitor added to the fibrinogen solution. As a specific example, and in some embodiments, the final concentration of bivalirudin in the buffer solution is about 0 mg/mL to about 0.05 mg/mL.

(b) Create the fibrinogen solution. A desired amount of fibrinogen is weighed out in a 1.7 mL tube, and the buffer made in operation (a) is added to the tube, followed by vortex mixing. Typically, the fibrinogen is in solution in about 30 seconds or less. The concentration of fibrinogen in the buffered solution can range from about 2% w/v to about 25% w/v, such as from about 3% w/v to about 25% w/v, such as from about 5% w/v to about 20% w/v, such as from about 10% w/v to about 15% w/v. With solutions having a concentration of fibrinogen of 5% w/v or more, degassing can be performed by, e.g., spinning the tube at about 10,000 relative centrifugal force (RCF) for several minutes using an Eppendorf tube (e.g., a 1.7 mL Eppendorf tube) in a centrifuge. Inhibitor, such as bivalirudin, can be added to the fibrinogen solution, such as from about 10 μL to about 25 of a ~5 mg/mL bivalirudin solution. As discussed above, and in some embodiments, the amount of inhibitor in the fibrinogen solution is about 2× or more (such as about 2×-10×, such as about 4× to about 5×) than the amount of inhibitor in the buffer. In some examples, particles generated from the example apparatus include about 2.5% w/v of fibrinogen when about 5% w/v of fibrinogen in buffered solution is used.

In addition, various biomaterials/macromers such as polyethylene glycol diacrylate (PEGDA), bovine serum albumin (BSA), hyaluronic acid, alginate, gelatin, and/or collagen can be added to the fibrinogen solution without affecting the stability and/or solubility of the fibrinogen solution. Supraphysiological amounts of fibrinogen can also be kept soluble and stable with these biomaterials/macromers. Table 1 shows various biomaterials/macromers that can be added to various example fibrinogen solutions without precipitation. These biomaterials/macromers can be used to alter the function of the fibrin gel, such as alteration of cell behavior, mechanical properties, and/or creating a more versatile platform for regenerative medicine.

TABLE 1

| Macromer | Macromer concentration, w/v | Fibrinogen concentration, w/v |
| --- | --- | --- |
| PEGDA, mw 700 Da | 8% | 5% |
| Alginate | 3% | 5% |
| Hyaluronic acid | 3% | 4% |
| Gelatin | 10% | 10% |

In some examples, transglutaminase Factor XIII can be added to the fibrinogen solution, for example about 0.5 international unit (IU) per mL (IU/mL) to about 2 IU/mL), such as about 1 IU/mL of transglutaminase Factor XIII can be added. Transglutaminase Factor XIII can be added to the fibrinogen solution to crosslink and stabilize the polymerized fibrin gel.

(c) Create the thrombin solution. A desired amount of thrombin is weighed out in a 1.7 mL tube, and the buffer made in operation (a), followed by vortex mixing. Typically, no inhibitor is added to the thrombin solution. In some embodiments, the concentration of thrombin in the thrombin solution ranges from about 0.2 IU/mL to about 2 IU/mL, such as from about 0.2 IU/mL to about 1 IU/mL, such as from about 0.4 IU/mL to about 0.6 IU/mL. In some embodiments, the concentration of thrombin in the thrombin solution ranges from about 0.5 IU/mL to about 2 IU/mL, such as from about 0.75 IU/mL to about 1.75 IU/mL, such as from about 1 IU/mL to about 1.5 IU/mL. In at least one example, the concentration of thrombin in the thrombin solution is about 2 IU to about 10 IU. The thrombin solution can be degassed in a similar fashion as that described above for the fibrinogen solution.

(d) Connect tubing. Tubing, or other suitable structure/device, is utilized to couple the fibrinogen solution, buffer, and thrombin solution to the microfluidic device.

(e) Flow the fluorocarbon oil. The microfluidic device is filled with a fluorocarbon oil by, e.g., positive pressure pumps. The fluorocarbon oil is flowed at a rate of about 2 μL/min or more, such as from about 3 μL/min to about 30 μL/min, such as from about 5 μL/min to about 30 μL/min, such as from about 10 μL/min to about 25 μL/min, such as from about 15 μL/min to about 20 μL/min.

(f) Commence flowing of the solutions. The buffer, fibrinogen solution, and thrombin solution flow into the microfluidic device at suitable flow rates. The buffer, fibrinogen solution, and thrombin solution can have a flow rate (e.g., initial flow rate, intermediate flow rate, or final flow rate) between about 0.5 μL/min to about 5 μL/min, such as from about 1 μL/min to about 4 μL/min, such as from about 2 μL/min to about 3 μL/min. In some examples the flow rate is about 0.5 μL/min to about 3 μL/min.

In some examples, the flow rates are adjusted such that the buffer, fibrinogen solution, and thrombin solution are flowing at approximately the same rate (e.g., the flow rates of the buffer, fibrinogen solution, and thrombin solution deviate less than about 10% from each other). In some examples, the flow rate of the fluorocarbon oil is about 2× to 3× that of the initial flow rate, intermediate flow rate, or final flow rate of the buffer, fibrinogen solution, and/or thrombin solution. The fluorocarbon oil is pushed out of the device as the aqueous phases enter the device, displacing the fluorocarbon oil from the device except for the oil-only channels.

(g) Independently adjust the flow rates of the buffer, fibrinogen solution, thrombin solution, and/or fluorocarbon oil. In some embodiments, the flow rate of the buffer is reduced while the flow rates of the fibrinogen solution and the thrombin solution are increased. By decreasing the flow rate of the buffer and increasing the flow rates of the fibrinogen solution and/or thrombin solution, the fibrinogen content in the particles/droplets can be adjusted. For example, the flow rate of the buffer is reduced to a flow rate of about 0.5 μL/min to about 3 μL/min, such as from about 1 μL/min to about 2 μL/min; the flow rate of the fibrinogen solution is increased to a flow rate of about 2 μL/min to about 5 μL/min, such as from about 3 μL/min to about 4 μL/min; and/or the flow rate of the thrombin solution is increased to a flow rate of about 2 μL/min to about 4 μL/min, such as from about 2.5 μL/min to about 3.5 μL/min or from about 2 μL/min to about 3 μL/min.

In other examples, the flow rate of one or more of the buffer, fibrinogen solution, thrombin solution, and fluorocarbon oil is adjusted while one or more of the buffer, fibrinogen solution, thrombin solution, and fluorocarbon oil is held constant. In some embodiments, the flow rate of the buffer, the flow rate of the fibrinogen solution, and/or flow rate of the thrombin solution are adjusted such that the flow rates of the buffer, the fibrinogen solution, and/or the thrombin solution deviate from one another by less than about 10%. In some embodiments, the flow rate of the buffer can be increased to drive the components in the microfluidic device out of the device. This can be performed when fibrin is forming in the device. In at least one embodiment, the fibrinogen content can be increased by, e.g., reducing the flow rate of the buffer to a low or negligible flow rate.

(h) Collection and Incubation. The particles/droplets in the fluorocarbon oil exit the microfluidic device and are collected in, e.g., a tube. The fibrinogen in the particles/droplets is then polymerized by, e.g., incubation. The temperature of the incubator is higher than room temperature (15-25° C.), such as about 25° C. or more, such as about 30° C. or more, such as from about 30° C. to about 37° C. The time of polymerization is about 1 hour or more such as from about 3 hours to about 24 hours, such as from about 5 hours to about 15 hours. As a result of the aforementioned operations, the particles/droplets now include fibrin.

(i) Filter and Wash. The particles in fluorocarbon oil are filtered with any suitable filter, such as a 0.22 μm membrane filter, and washed with a suitable aqueous solution (such as PBS) to remove the fluorocarbon oil, fluorosurfactant, and any other components or materials. For quantification and study, the filter can then be inverted and the particles placed into a sterile tissue culture six-well plate.

Unless the context indicates otherwise, the operations described above can be performed at a temperature of about room temperature (e.g., from about 15° C. to about 25° C.) or at a temperature from about 0° C. to about 25° C. The order of operations can be altered.

In an illustrative, but non-limiting example, the particles can be formed using a fibrinogen solution (~5% weight/volume fibrinogen in a solution of ~50 mM arginine and ~50 mM glutamic acid in PBS, pH~7-9, 0.125 mg/mL bivalirudin), a thrombin solution (~10 U/ml thrombin in a solution of ~50 mM arginine and ~50 mM glutamic acid in PBS, pH~7.5), and a buffer (~50 mM arginine and ~50 mM glutamic acid in PBS, pH~7.5, with ~0.05 mg/mL bivalirudin). These three solutions are introduced to the microfluidic device, along with Novec Oil (with a surfactant, such as RAN Biotech 008 in Fluorinert™ FC-40 or Picosurf™ 2). Once the flows of the fluorocarbon oil, fibrinogen solution, thrombin solution, and buffer are stable, the flow rate of fluorocarbon oil is adjusted to about 9-10 μL/min, the flow rate of the fibrinogen solution is adjusted to about 3-4 μL/min, the flow rate of the thrombin solution is adjusted to about 2-3 μL/min, and the flow rate of the buffer is adjusted to about 0.5-1 μL/min. Droplets are pinched off by the Novec oil with surfactant. The droplets are collected from the microfluidic device and placed in an incubator at ~37° C. to form fibrin particles.

As discussed above, fibrin polymerizes extremely rapidly. While advantageous for maintaining hemostasis, this can present a challenge when working with fibrinogen/thrombin solutions. The rapid polymerization and poor solubility of fibrinogen has prevented widespread use of fibrin as a scaffold for tissue engineering compared to similar naturally-derived polymers such as collagen and gelatin. In fact, the enzyme unit definition thrombin, the catalytic fibrinogen polymerization enzyme, is based on the amount of thrombin capable of gelling a 1 ml of human plasma in 15 seconds. This rapid polymerization is one of the issues that has all but prevented fibrin from being used in a microfluidic device where the rapid gelation can fill and/or clog micron-scale channels.

The embodiments described herein overcome these challenges by enabling, e.g., control over the chemistry of reaction components and the polymerization as well as selective tuning of flow rates of the solutions flowing through the microfluidic device. The example apparatus and methods described herein advantageously provide, e.g., high resistance to clogging of the microfluidic device even when high concentrations of polymerizable fibrinogen and/or large quantities of thrombin are utilized.

Figure 2:
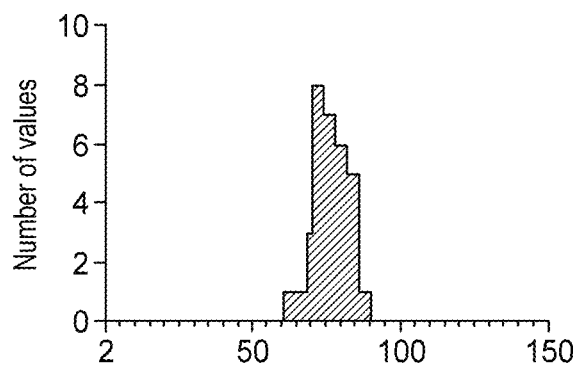
FIG. 2 shows exemplary data illustrating the size distribution of example particles formed using one or more embodiments described herein.
Figure 3A:
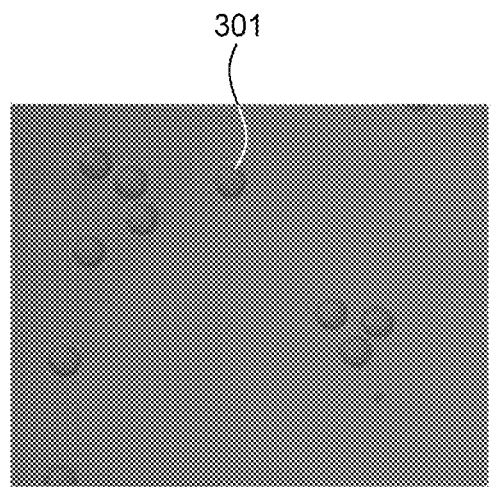
FIG. 3A is an exemplary image of example particles formed using embodiments described herein (Scale: 100 μm).
Figure 3B:
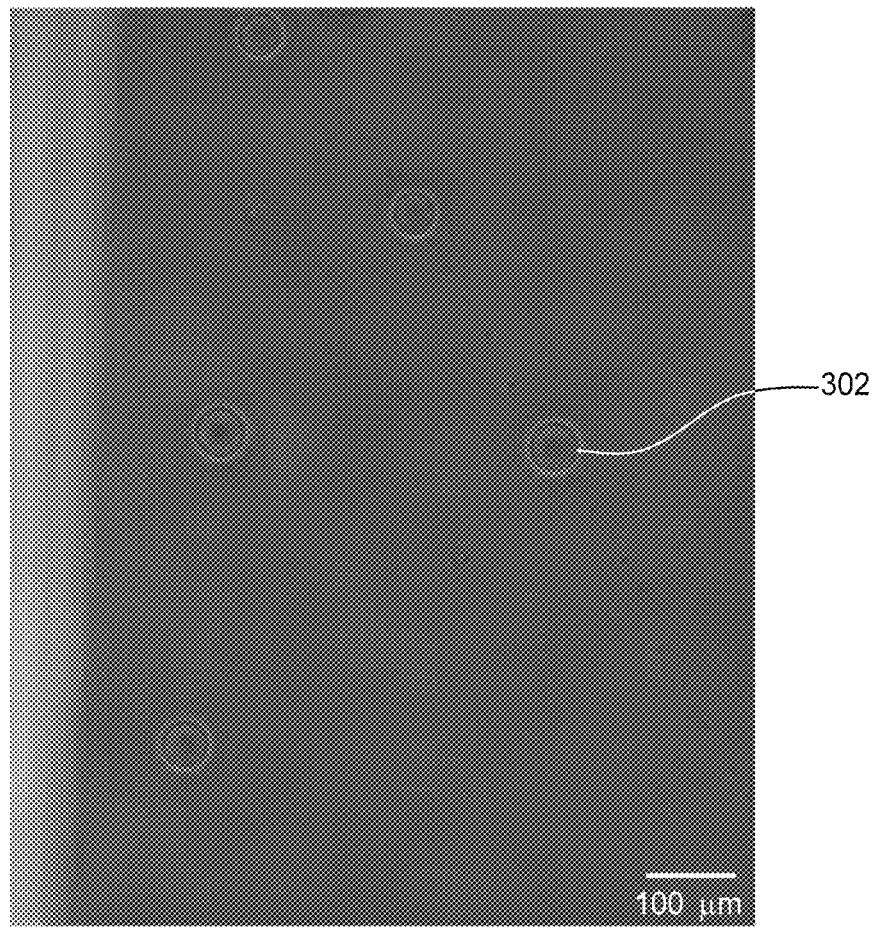
FIG. 3B is an exemplary image of example particles formed using one or more embodiments described herein (Scale: 100 μm).

FIG. 2 shows exemplary data illustrating the size distribution of particles/droplets generated according to embodiments described herein. Images were quantified using ImageJ (National Institutes of Health). The results show a tight distribution (highly monodispersed) of median particle size ranging from about 60 μm to about 90 μm (in mean diameter). FIG. 3A and FIG. 3B are exemplary images of example fibrin particles 301 and 302 after collection and fibrin polymerization. In both images, a mean diameter of the particles is about 50 μm. The results show the superior homogeneity of the fibrin particles as compared to the inconsistently-sized fibrin particles formed by conventional methods such as through sonication or the use of polystyrene beads.

The dimensions of the fluidic channel 103 and the flow rates of the various components entering the microfluidic device 101, among other parameters, can be adjusted to increase or decrease the size of the particles. Accordingly, and in some embodiments, the size (in mean diameter) of the particles is about 15 μm or more, such as from about 25 μm to about 150 μm, such as from about 50 μm to about 125 μm, such as from about 75 μm to about 100 μm.

Figure 4:
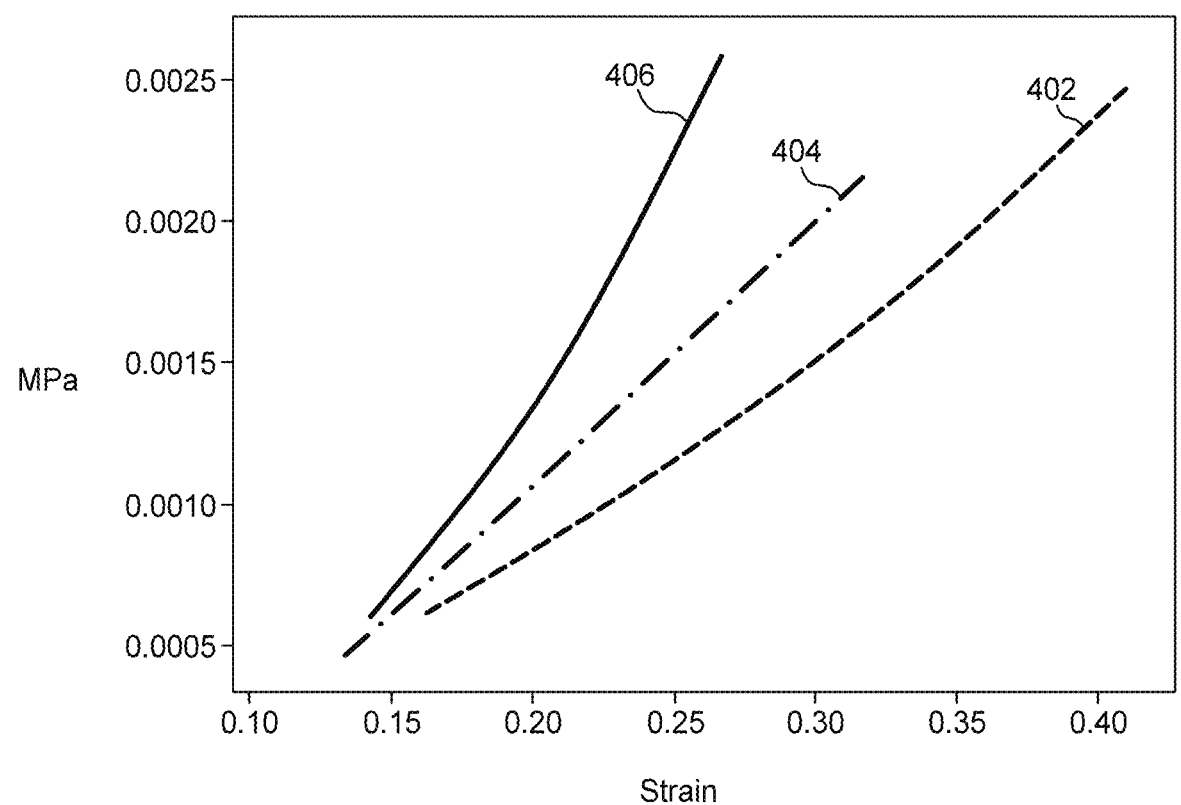
FIG. 4 shows exemplary data illustrating mechanical properties of supraphysiological fibrin formed using one or more embodiments described herein.

FIG. 4 shows exemplary data illustrating mechanical properties of supraphysiological fibrin formed using embodiments described herein. Three examples of polymerized supraphysiological fibrin are shown as weight polymerized fibrin to volume of fibrinogen solution. The examples are 1.5% w/v (Ex. 402), 3% w/v (Ex. 404), and 6% w/v (Ex. 406). Bulk mechanical testing data was performed on 5 mm×7 mm diameter sections using a TA Instruments Q800™ Dynamic Mechanical Analyzer. Ex. 402, Ex. 404, and Ex. 406, have a strain of about 6.3 kPa, about 9 kPa, and about 20 kPa, respectively. The data illustrates that, e.g., one or more mechanical properties of the polymerized fibrin can be modulated according to embodiments described herein. As such, the supraphysiological fibrin can be mechanically tuned to a greater degree of strain than physiological fibrin.

Example Applications

Due to, at least, the slowing of polymerization of fibrinogen to fibrin and being able to tune the mechanical properties of the fibrin gel, the inventors have also enabled applications of this material, such as biologically-active scaffolds with tunable mechanical properties. Briefly, the scaffolds are made utilizing fibrin particles and one or more polymers, such as biocompatible polymers. Upon exposure to ultraviolet (UV) light, the one or more polymers degrade, leaving a scaffold comprising a fibrin network.

Fibrin may be used to create tissue scaffolds for regenerative medicine due to its high cell adhesion, growth factor absorption, and the body's natural mechanisms to degrade and remodel fibrin. Fibrin, while highly elastic, is not dense enough to achieve a high elastic modulus. However, by increasing the content of the free fibrinogen beyond physiological ranges as disclosed herein, the mechanical properties can be tuned. Further, by delaying the polymerization to ensure proper mixing of thrombin in the free fibrinogen, a homogenous scaffold can be created. Delaying the polymerization with, e.g., bivalirudin, enables pouring, flowing, or otherwise manipulating the fibrinogen solution without the deleterious effects of rapid gelation. This enables the creation of complicated, rigid shapes comprising fibrin. Fibrin-based scaffolds may be used to replace the multitude of natural or synthetic materials such as collagen, alginate, polyacrylic acid, polypropylene, fumarate, polypropylene fumarate, etc. currently utilized for tissue scaffolds.

In some embodiments, a fibrin scaffold can be made using fibrin particles and polymer particles. The polymer can be a biocompatible polymer, such as poly(ethylene glycol) diphotodegradable acrylate (PEGdiPDA). PEGdiPDA is both photopolymerizable and photodegradable at certain wavelengths of ultraviolet (UV) light, polymerizing at a wavelength of about 405 nm and degrading at a wavelength of about 365 nm.

The polymer(s) used to make the scaffold can be of various sizes and/or chemical architectures depending on the application. Moreover, the polymer can have permeability properties and/or degradation properties useful for, e.g., release of pharmaceuticals. Various compounds, including those having acryl groups, can be covalently polymerized to form the PEGdiPDA network. The acryl group is a radical electron donor and reacts with another acryl group to polymerize the gel.

Figure 5B:
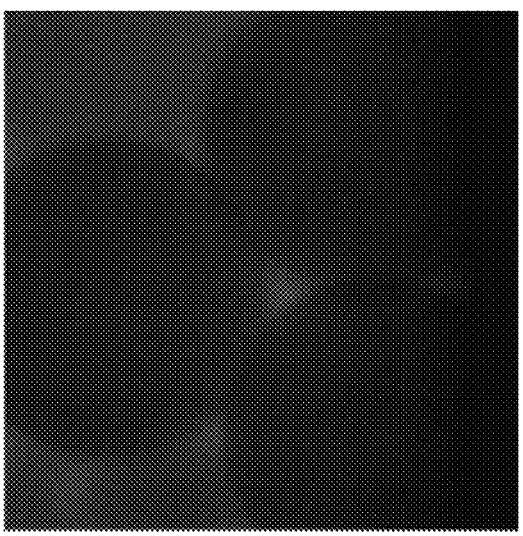
FIG. 5B is an enlarged image showing a portion of FIG. 5A according to at least one embodiment of the present disclosure (Scale: 50 μm).
Figure 5D:
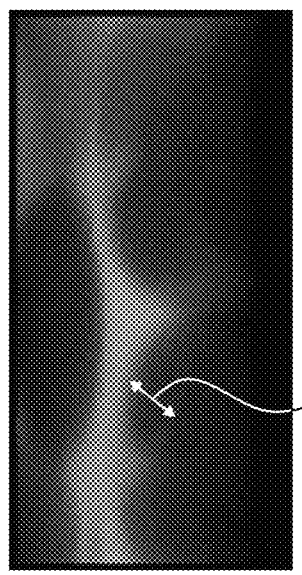
FIG. 5D is an enlarged image showing a portion of FIG. 5C according to at least one embodiment of the present disclosure (Scale: 50 μm).
Figure 5A:
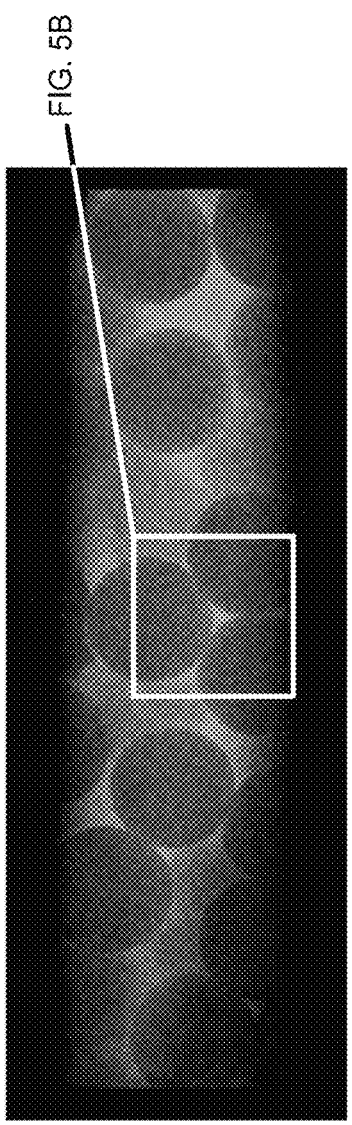
FIG. 5A is an exemplary image of an example acryl-rhodamine-labeled (red) poly(ethylene glycol) diphotodegradable acrylate (PEGdiPDA) microparticles in a fibrin gel (green) according to at least one embodiment of the present disclosure (Scale: 100 μm).

In the following non-limiting procedure, the scaffold of fibrin and polymer can be formed using a single aqueous phase droplet generator that works in an analogous fashion to the three aqueous phase fibrin droplet generator described above. The PEGdiPDA particles are mixed with a ~6% fibrinogen solution with bivalirudin and thrombin, then injected into a single aqueous phase droplet generator with a depth of 125 μm, a width of 3 μm, and a length of about 1 cm, and allowed to fully polymerize over about 2 hours at 37° C. The PEGdiPDA is also polymerized with a radical electron donor upon exposure to UV light (~405 nm). FIG. 5A is an exemplary image of example acryl-rhodamine-labeled (red) PEGdiPDA microparticles in a fibrin gel (green). Imaging was performed using an Olympus IX-71™ microscope, a Phantom high speed camera, and illuminated with a X-Cite™ 120 LED illumination source. FIG. 5B is an enlarged image showing a portion of FIG. 5A. As shown, monodisperse PEGdiPDA particles can be created, collected, and then polymerized using a radical electron donor that is active when exposed to about 405 nm UV light.

Voids can then be made in the fibrin matrix by degrading the PEGdiPDA polymer using UV light. For this non-limiting example, the scaffold of fibrin and polymer particles are exposed to UV light (365 nm) to degrade the PEGdiPDA polymer particles, leaving a dense, polymerized fibrin network with large voids.

Figure 5C:
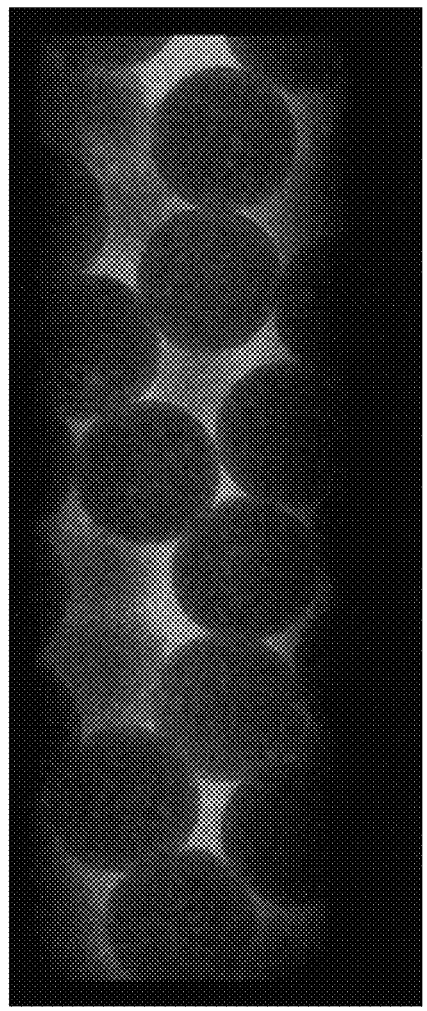
FIG. 5C is an exemplary image of the example shown in FIG. 5A after degradation of the PEGdiPDA portion according to at least one embodiment of the present disclosure (Scale: 100 μm).

FIG. 5C is an exemplary image of the example shown in FIG. 5A after degradation of the PEGdiPDA portion. FIG. 5D is an enlarged image showing a portion of FIG. 5C. The high-concentration fibrin-matrices are rigid and retain a void even when the fibrin particles are degraded. The results indicate that the fibrin network of supraphysiological levels of fibrin exhibit robust mechanical properties, in that when the PEGdiPDA particles degrade, the fibrin network does not shift or collapse in on itself. Moreover, the results indicate the versatility of the fibrin network for tissue engineering applications. Depending on the size or type of polymer used, a variety of size-controlled voids in the fibrin matrix can be formed.

Embodiments described herein generally relate to compositions comprising fibrin and to methods of forming such compositions. Such embodiments provide, at least, certain advantages over conventional methods. For example, device-clogging is minimized and the amount of fibrin (as well as the mechanical properties of the fibrin) formed is easily modulated by utilizing the embodiments described herein. All operations can be performed at about room temperature, such that low temperatures are not used (although certain operations can be performed at low temperatures, if desired. Further, no harsh solvents are used for particle recovery (although some embodiments can include the use of such solvents).

All documents described herein are incorporated by reference herein, including any priority documents and/or testing procedures to the extent they are not inconsistent with this text. In the foregoing, reference is made to embodiments of the disclosure. However, it should be understood that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the foregoing aspects, features, embodiments and advantages are merely illustrative and are not considered elements or limitations of the appended claims except where explicitly recited in a claim(s). Likewise, reference to "the disclosure" shall not be construed as a generalization of any inventive subject matter disclosed herein and shall not be considered to be an element or limitation of the appended claims except where explicitly recited in a claim(s). Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa.

As used herein, a "composition" can include component(s) of the composition and/or reaction product(s) of two or more components of the composition.

The term "coupled" is used herein to refer to elements that are either directly connected or connected through one or more intervening elements. For example, an opening can be directly connected to the fluidic channel, or it can be connected to the fluidic channel via intervening elements.

For purposes of this present disclosure, and unless otherwise specified, all numerical values within the detailed description and the claims herein are modified by "about" or "approximately" the indicated value, and consider experimental error and variations that would be expected by a person having ordinary skill in the art. For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

As used herein, the indefinite article "a" or "an" shall mean "at least one" unless specified to the contrary or the context clearly indicates otherwise. For example, aspects comprising "a monomer" include aspects comprising one, two, or more monomers, unless specified to the contrary or the context clearly indicates only one monomer is included.

While the foregoing is directed to embodiments of the present disclosure, other and further embodiments of the disclosure may be devised without departing from the basic scope thereof, and the scope thereof is determined by the claims that follow.

What is claimed is:

1. A method of forming fibrin particles, comprising:
   (a) introducing a buffer, a fibrinogen solution, and a thrombin solution to a first end of a microfluidic device to form a mixture, the buffer comprising amino acids, the amino acids comprising:
      a first amino acid having a side chain group that is positively charged at a pH of 7; and
      a second amino acid having a side chain group that is negatively charged at a pH of 7;
   (b) contacting the mixture with a fluorocarbon oil and a surfactant to form fibrinogen-containing particles;
   (c) applying positive pressure to the microfluidic device to cause the fibrinogen-containing particles to flow towards a second end of the microfluidic device;
   performing (a), (b), and (c) at a temperature that is from about 15° C. to about 25° C.;
   collecting the fibrinogen-containing particles from the second end of the microfluidic device; and
   polymerizing the fibrinogen-containing particles to form fibrin particles after the fibrinogen-containing particles are collected from the microfluidic device.

2. The method of claim 1, further comprising:
   adjusting a flow rate of the buffer, a flow rate of the fibrinogen solution, a flow rate of the thrombin solution, or a combination thereof;
   adjusting a flow rate of the fluorocarbon oil and surfactant; or
   reducing the flow rate of the buffer while increasing the flow rate of the fibrinogen solution, the flow rate of the thrombin solution, or both.

3. The method of claim 1, wherein:
   the first amino acid comprises arginine, lysine, histidine, or combinations thereof;
   the second amino acid comprises aspartic acid, glutamic acid, or combinations thereof;
   the fibrinogen solution, the buffer, or both, comprise an inhibitor, the inhibitor comprising a fibrinogen polymerization inhibitor, a thrombin inhibitor, or combinations thereof; or
   a combination thereof.

4. The method of claim 3, wherein the inhibitor comprises bivalirudin.

5. The method of claim 1, wherein:
   the first amino acid comprises arginine, lysine, histidine, or combinations thereof; and
   the second amino acid comprises aspartic acid, glutamic acid, or combinations thereof.

6. The method of claim 1, wherein:
   a concentration of the first and second amino acids in the buffer is from about 10 mM to about 100 mM;
   a concentration of thrombin in the thrombin solution is from about 0.5 IU/mL to about 2 IU/mL; or
   a combination thereof.

7. The method of claim 1, wherein an amount of fibrinogen in the fibrinogen solution is 5% w/v or more.

8. The method of claim 7, wherein:
   the amount of fibrinogen in the fibrinogen solution is from about 5% w/v to about 20% w/v; and
   a concentration of the first and second amino acids in the buffer is from about 25 mM to about 100 mM.

9. The method of claim 1, wherein:
   a concentration of the first and second amino acids in the buffer is from about 25 mM to about 75 mM;
   the first amino acid comprises arginine; and
   the second amino acid comprises glutamic acid.

10. The method of claim 1, wherein a median diameter of the fibrinogen-containing particles is from about 15 μm to about 125 μm.

11. The method of claim 1, wherein the microfluidic device is substantially free of fibrin.

12. The method of claim 1, wherein an amount of fibrin in the fibrin particles is greater than about 1% w/v.

13. A method of forming fibrin particles, comprising:
   (a) co-flowing a buffer, a fibrinogen solution, and a thrombin solution into an introduction area of a fluidic channel to form an aqueous phase, the fluidic channel further comprising a contacting area and a mixing area, the contacting area disposed between the introduction area and mixing area, wherein:
      the buffer comprises amino acids, the amino acids comprising:
         a first amino acid having a side chain group that is positively charged at a pH of 7; and
         a second amino acid having a side chain group that is negatively charged at a pH of 7; and
      the fibrinogen solution, the buffer, or both, comprise an inhibitor, the inhibitor comprising a fibrinogen polymerization inhibitor, a thrombin inhibitor, or combinations thereof;
   (b) causing the aqueous phase to flow from the introduction area of the fluidic channel to the contacting area of the fluidic channel; contacting area in a location between the introduction area and mixing area;
   (c) contacting the aqueous phase with an oil phase comprising a fluorocarbon oil and a surfactant at the contacting area to form a dispersion of the aqueous phase in the oil phase, the dispersion comprising fibrinogen-containing particles;
   performing (a), (b), and (c) at a temperature that is from about 15° C. to about 25° C.;
   causing the dispersion to flow from the contacting area to the mixing area and to a fluidic channel exit;
   collecting the dispersion comprising the fibrinogen-containing particles from the fluidic channel exit; and
   heating the dispersion comprising the fibrinogen-containing particles under conditions effective to form fibrin particles after the fibrinogen-containing particles exit the fluidic channel.

14. The method of claim 13, further comprising:
   adjusting a flow rate of the buffer, a flow rate of the fibrinogen solution, a flow rate of the thrombin solution, or a combination thereof to flow rates of the buffer, the fibrinogen solution, and the thrombin solution, or a combination thereof that deviate from one another by less than about 10%;
   adjusting a flow rate of the fluorocarbon oil and surfactant; or
   reducing the flow rate of the buffer while increasing the flow rate of the fibrinogen solution, the flow rate of the thrombin solution, or both.

15. The method of claim 13, wherein:
   the first amino acid comprises arginine, lysine, histidine, or combinations thereof; and
   the second amino acid comprises aspartic acid, glutamic acid, or combinations thereof.

16. The method of claim 13, wherein:
a concentration of the first and second amino acids in the buffer is from about 25 mM to about 100 mM;
a concentration of thrombin in the thrombin solution is from about 0.5 IU/mL to about 2 IU/mL;
or a combination thereof.

17. The method of claim 13, wherein an amount of fibrinogen in the fibrinogen solution is from about 2% w/v to about 25% w/v.

18. A method of forming fibrinogen-containing particles, comprising:
(a) co-flowing a buffer, a fibrinogen solution, a thrombin solution to form an aqueous phase, wherein:
an amount of fibrinogen in the fibrinogen solution is from about 5% w/v to about 25% w/v;
the buffer comprises amino acids, the amino acids comprising:
a first amino acid having a side chain group that is positively charged at a pH of 7; and
a second amino acid having a side chain group that is negatively charged at a pH of 7; and
the fibrinogen solution, the buffer, or both, comprise an inhibitor, the inhibitor comprising bivalirudin; and
(b) contacting the aqueous phase with an oil phase comprising a surfactant to form fibrinogen containing droplets, wherein (a) and (b) are performed at a temperature that is from about 15° C. to about 25° C.

19. The method of claim 18, wherein:
the first amino acid comprises arginine, lysine, histidine, or combinations thereof; and
the second amino acid comprises aspartic acid, glutamic acid, or combinations thereof.

20. The method of claim 18, wherein a concentration of the first and second amino acids in the buffer is from about 25 mM to about 100 mM.

* * * * *